United States Patent
Yoo et al.

(10) Patent No.: US 6,723,798 B1
(45) Date of Patent: Apr. 20, 2004

(54) RESINS HAVING VINYL ETHER LINKER FOR THE SOLID PHASE ORGANIC SYNTHESIS

(75) Inventors: SungEun Yoo, Chungchongnam-do (KR); YoungDae Gong, Daejeon (KR); JinSoo Seo, Daejeon (KR)

(73) Assignee: Korean Research Institute of Chemical Technology (KR)

( * ) Notice: Subject to any disclaimer, the term of this patent is extended or adjusted under 35 U.S.C. 154(b) by 0 days.

(21) Appl. No.: 10/111,671
(22) PCT Filed: Aug. 28, 2000
(86) PCT No.: PCT/KR00/00962
§ 371 (c)(1),
(2), (4) Date: Apr. 26, 2002
(87) PCT Pub. No.: WO02/18455
PCT Pub. Date: Mar. 7, 2002

(51) Int. Cl.$^7$ .................................................. G08F 8/00
(52) U.S. Cl. ................................. 525/332.2; 525/333.4; 525/384
(58) Field of Search .............................. 525/333.4, 384, 525/332.2

(56) References Cited

PUBLICATIONS

"A New Vinyl Ether Type Linker for Solid–Phase Synthesis," Yoo et al, Tetrahedron Letters (2000), 41(33), 6415–6418, Aug. 12, 2000.*

\* cited by examiner

*Primary Examiner*—Bernard Lipman
(74) *Attorney, Agent, or Firm*—Finnegan, Henderson, Farabow, Garrett & Dunner, L.L.P.

(57) ABSTRACT

The present invention relates to a resin having a vinyl ether linker and more particularly, to a resin having a vinyl ether linker expressed by formula (I), useful for the synthesis of compounds having hetero atoms such as alcohol, thiol, imidazole, triazole and tetrazole by employing combinatorial chemical synthesis on solid supports.

13 Claims, No Drawings

RESINS HAVING VINYL ETHER LINKER FOR THE SOLID PHASE ORGANIC SYNTHESIS

BACKGROUND OF THE INVENTION

Field of the Invention

The present invention relates to a resin having a vinyl ether linker and more particularly, to a resin having a vinyl ether linker expressed by the following formula (1), useful for the synthesis of compounds having hetero atoms such as alcohol, thiol, imidazole, triazole and tetrazole by employing combinatorial chemical synthesis on solid supports,

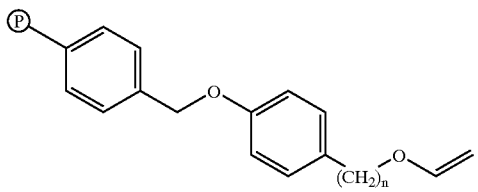

(1)

wherein Ⓟ is polystyrene-divinyl benzene; and n is an integer of 1 to 5.

Combinatorial chemical synthesis (CCS) is one of the important new methodologies to produce a diverse family of compounds simultaneously in the development of new compounds and new materials, while traditional chemical synthesis relied on one product from one reaction. CCS has become a powerful tool for rapidly discovering new lead compounds and optimizing molecular structures and properties thereof. Within the past several years, a number of reports have appeared that combinatorial chemistry using solid-phase chemical synthesis provides great potential, because solid-phase chemistry have several big advantages to develop combinatorial techniques such as possible to make a lot of libraries in one pot, simple to purify, simple to simultaneous multi step reaction, and possible to automation of reaction process, thus applicable for High Throughput Screening (HTS).

As explained above, CCS overcomes the uneconomicity and ineffectiveness of the conventional synthetic technologies but nevertheless it was seldom applied in the organic synthesis due to decreases in reaction rate and reactivity with using of solid support.

Linker moiety attaching between the compound and the solid-phase support has been introduced in order to solve such problems of decreases in reaction rate and reactivity in the performing CCS on the solid support. Large numbers of linkers have been developed and applied in the solid-phase support synthesis. Among those, 3,4-dihydro-2H-pyran-2-yl-methanol (DHP) linker is preferred as both linker and protecting group because it is facilitated for introduction and cleavage of alcohol, thiol, imidazole, triazole or tetrazole group. However, DHP linker is expensive and thus, it is difficult to apply for industrial manufacturing process.

SUMMARY OF THE INVENTION

Introduction of vinyl ether linker, which is facilitated to attach and detach pharmacologically active compounds such as alcohol, thiol, imidazole, triazole, or tetrazoleis, to Merrifield resin, which is a solid support, provides excellent utility value in the organic synthesis on solid-phase support.

Accordingly, an object of the present invention is to provide a resin having a vinyl ether liker which is also a protecting group.

In accordance with one aspect of the present invention, there is provided a method for preparing a resin having vinyl ether liker. Another object of the present invention is to provide a process for preparing hetero atom-containing compounds such as alcohols, thiols, triazoles and tetrazoles by employing the resin having vinyl ether linker of the present invention as a solid-phase support in Combinatorial chemistry synthesis.

DETAILED DESCRIPTION OF THE INVENTION

The present invention provides a resin having vinyl ether linker of formula (1) which is useful for combinatorial chemical synthesis,

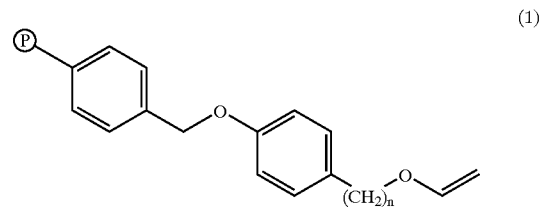

(1)

wherein Ⓟ is polystyrene-divinyl benzene; and n is an integer of 1 to 5.

The present invention is described in more detail as set forth hereunder. The resin having vinyl ether linker of the present invention is prepared as the following 3-steps comprising:

(1) a reduction of methyl (4-hydroxybenzyl)ester of formula (2) to 4-hydroxylphenethyl alcohol of formula (3),

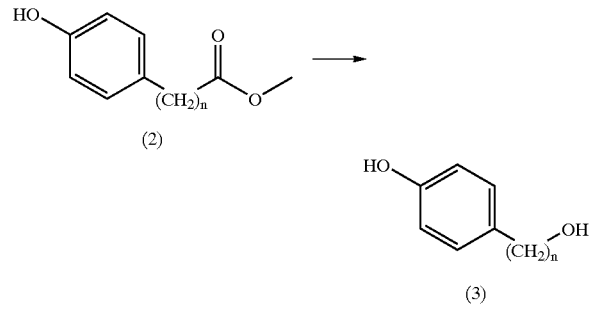

wherein the reduction is performed by adding excess amount of a typical reducing agent, preferably 2.0 equivalent of lithium aluminum hydride or diisopropylaluminum hydride at 0° C. and then stirring at room temperature in a typical aprotic organic solvent such as tetrahydrofuran;

(2) a reaction of the obtained compound of formula (3) with ethylvinyl ether of formula (4) to produce 4-(2-vinyloxyethyl)phenol of formula (5),

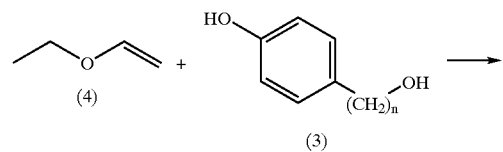

-continued

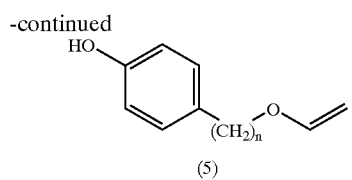

(5)

wherein the phenethyl alcohol of formula (3) is reacted with ethylvinyl ether of formula (4) in the presence of mercury catalyst at room temperature; and (3) a reaction of the obtained compound of formula (5) with Merrifield resin of formula (6) to produce the desired product resin having vinyl ether linker of formula (1),

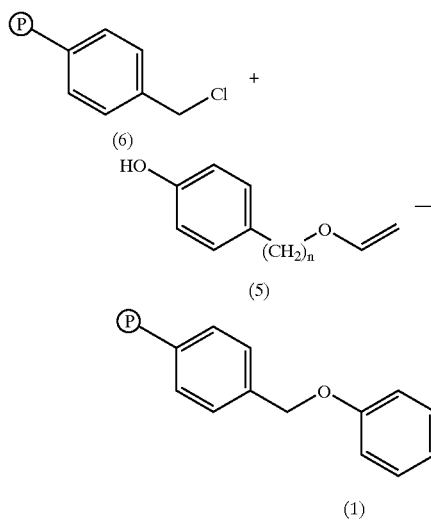

wherein the reaction is performed in the presence of a base catalyst such as sodium alkoxide and sodium hydride in a typical polar solvent such as dimethylacetamide at 50° C. and after the reaction was performed, no residual Merrifield resin was detected, which was identified by the nonexistence of peak corresponding to chlorine atom (Cl) in the X-ray photoelectron spectroscopy (XPS) element analysis.

More detailed reaction condition and the relative elemental analysis results are given in Example 1.

The present invention further provides an application of the resin having vinyl ether linker of formula (1) as a solid-phase support to CCS. A preferred example is a preparation of hetero atom-containing compounds of formula (7), HY—(CH$_2$)$_m$—X  (7)

wherein Y is O or N;

X is H, OH, SH, a halogen atom, phenyl, phenyl or biphenyl substituted with halogen atom(s), or

formed by bonding another hetero atom (X') with Y, where Y and X' are independently hetero atom(s), of which number is 1 to 5, and bonded $C_1$–$C_4$ alkylene or alkenyl; and M is an integer of 1 to 4.

The following scheme 1 shows a process of introducing the hetero atom-containing compound of formula (7) to the resin having vinyl ether linker of formula (1) on a solid-phase support and a process for cleaving the same from the solid-phase support,

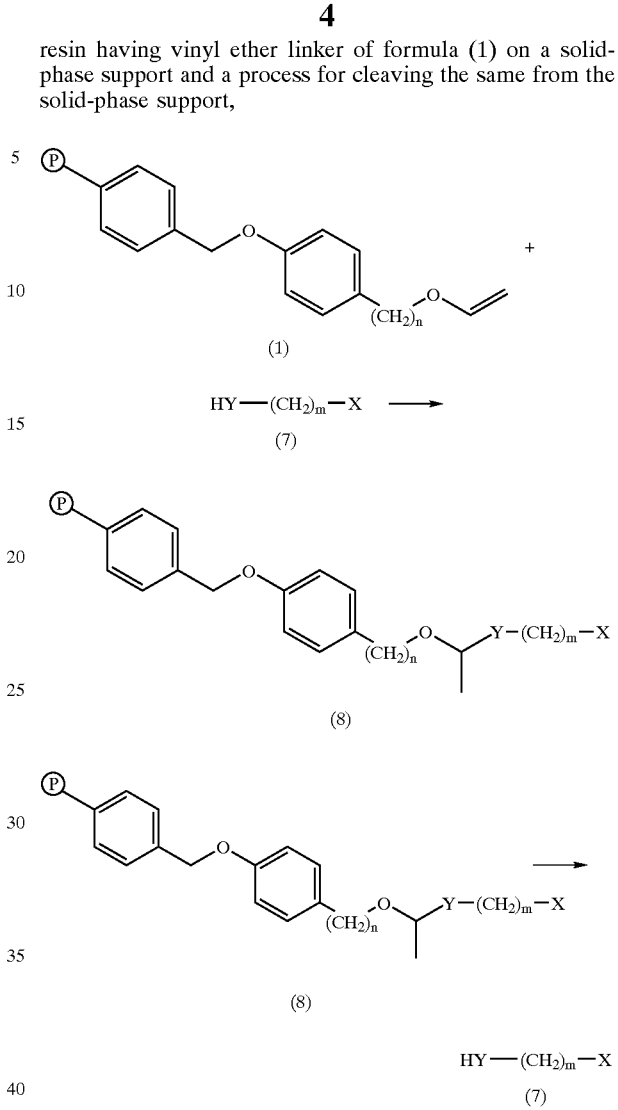

wherein Ⓟ, X, Y, n and m are previously defined.

In Scheme 1, the introduction of the hetero atom-containing compound of formula (7) to the resin having vinyl ether linker of formula (1) on a solid-phase support is performed in the presence of an acid catalyst chosen from camphorsulfonic acid, trifluoroacetic acid and pyridinium ρ-toluenesulfonate in 1,2-dichloroethane. Particularly, when the compound of formula (7) contains O or S, it is preferred to perform the reaction in the presence of pyridinium ρ-toluenesulfonate and when the compound of formula (7) contains N, it is preferred to perform the reaction in the presence of camphorsulfonic acid or trifluoroacetic acid. The compound of formula (7) is preferably used in the range of from 3 to 5 equivalents based to the compound of formula (1) and the formation of the compound (8) is indirectly identified by detecting disappearance of olefin peak, which is shown in the compound of formula (1), in IR spectrum.

After performing various organic reactions on solid-phase support, the cleavage reaction of the hetero atom-containing compound from the solid support is carried in the presence of excess amount of an acid and solvent, preferably HCl/methanol, at room temperature. The production of the hetero atom-containing compound is identified by IR, NMR, and Mass spectrographic analyses. More detailed reaction conditions for introduction and cleavage of the hetero atom-containing compound of formula (7) to/from the resin having vinyl ether linker of formula (1) on a solid-phase support and the relative elemental analysis results are given in Examples 2 and 3.

As described above, the resin having vinyl ether linker is a novel solid support useful for organic syntheses due to simple introduction and cleavage of compounds containing alcohol, thiol, imidazole, triazole, or tetrazole.

The following examples are intended to further illustrate the present invention without limiting its scope.

EXAMPLE 1

Preparation of Resin having Vinyl Ether Linker of Formula (1)

i) Preparation of 4-hydroxyphenethyl alcohol of formula (3a)

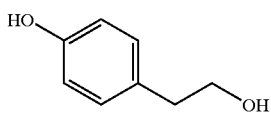

(3a)

Methyl-4-hydroxyphenyl acetate (23.0 g, 139.0 mmol) was dissolved in THF (400 ml). After cooling to 0° C., lithium aluminum hydride (LAH; 7.9 g, 209.0 mmol) was added over 1 hr, stirred for 2 hrs at 0° C. and additionally for 8 hrs at room temperature. 1N aqueous HCl (300 ml) was added at 0° C. and the reaction mixture was extracted with ethylacetate (200 ml×3). The combined organic layer was washed with water (200 ml×2) and sat. NaCl (200 ml) and dried over $MgSO_4$. The dried organic layer was evaporated and the residue was purified by fresh column chromatography on silica gel (hexane/ethylacetate=3/1, v/v) to obtain white solid of the desired product, 4-hydroxyphenethyl alcohol (16.3 g, 118.0 mmol, yield 85%).

$^1$H NMR (200 MHz, $CDCl_3$): δ 7.10 (d, 2H, J=8.6 Hz), 6.78 (d, 2H, J=8.4 Hz), 4.96 (s, 1H), 3.83 (t, 2H, J=6.6 Hz), 2.81 (t, 2H, J=6.6 Hz).

ii) Preparation of 4-(2-vinyloxyethyl)phenol of Formula (5a)

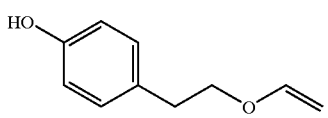

(5a)

4-Hydroxyphenethyl alcohol of formula 3a (15.0 g, 108.0 mmol) was added to ethylvinyl ether of formula 4(200 ml) and stirred for 20 minutes. After cooling to 0° C., mercury acetate (3.4 g, 10.8 mmol) was added and the reaction mixture was stirred for 24 hrs at room temperature. After evaporating solvent, the residue was purified by fresh column chromatography on silica gel (hexane/ethylacetate=5/1, v/v) to obtain pale yellow liquid of the desired product, 4-(2-vinyloxyethyl)phenol of formula 5a (11.0 g, 65 mmol, yield 60%).

$^1$H NMR (200 MHz, $CDCl_3$): δ 7.08 (d, 2H, J=8.8 Hz), 6.76 (d, 2H, J=8.6 Hz), 6.46 (dd, 1H, J=14.0, 6.8 Hz), 4.20 (dd, 1H, J=14.0, 2.0 Hz), 4.01 (dd, 1H, J=6.0, 2.0 Hz)

iii) Preparation of Resin Having Vinyl Ether Linker of Formula (1a)

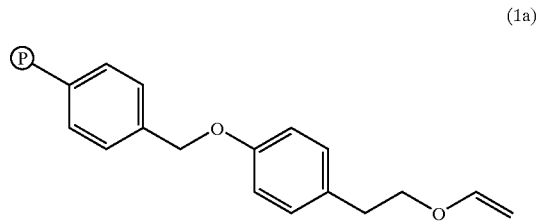

(1a)

To 4-(2-vinyloxyethyl)phenol (3.0 g, 18.0 mmol) in dimehtylacetamide (25 ml) was added sodium hydride (720.0 mg, 18.0 mmol). After the reaction mixture was stirred for 30 minutes at room temperature, Merrifield resin (2 mmol/g, 3.0 g, 6.0 mmol) was added and stirred for 24 hrs at 50° C.. The reaction mixture was filtered, washed with $CH_2Cl_2$, DMF, DMF/$H_2O$, $H_2O$ and MeOH several times, and dried to obtain light brown resin of the desired product of formula 1a (4.08 g).

IR(KBr): 1600, 1491, 1449, 1209, 1191, 1013 $cm^{-1}$

EXAMPLE 2

Introduction and Cleavage of Alcohol to/from Resin Having Vinyl Ether Linker i-1) Introduction of 4-bromobenzyl Alcohol

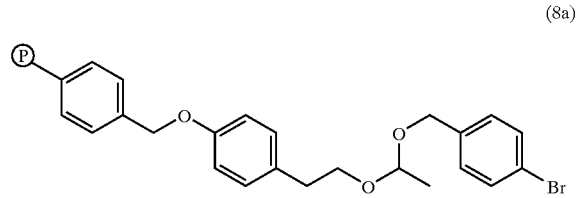

(8a)

To vinyl ether resin of formula 1a (340.0 mg, 0.5 mmol) in 1,2-dichloroethane (8 ml) was added pyridinium p-toulenesulfonate (25.0 mg, 0.1 mmol). 4-Bromobenyl alcohol (280.0 mg, 1.5 mmol) was added and stirred for 24 hrs at room temperature. The reaction mixture was filtered, washed with $CH_2Cl_2$, DMF, DMF/$H_2O$, $H_2O$ and MeOH several times, and dried to obtain light brown solid resin of the desired product of formula 8a (392 mg).

i-2) Cleavage of 4-bromobenzyl Alcohol of Formula (8a)

The obtained resin of formula 8a (392.0 mg) was added to 1.5% HCl/MeOH solution (15 ml) and stirred for 5 hrs at room temperature. The reaction mixture was filtered and filtrate was evaporated to obtain 4-bromobenyl alcohol (57.0 mg, yield 61%; 3-steps from Merrifield resin).

$^1$H NMR(200 MHz, $CDCl_3$): δ 7.48 (d, 2H, J=8.4 Hz), 7.24 (d, 2H, J=8.8 Hz), 4.65 (s, 2H)

ii-1) Introduction of 1-phenyl-2-propanol

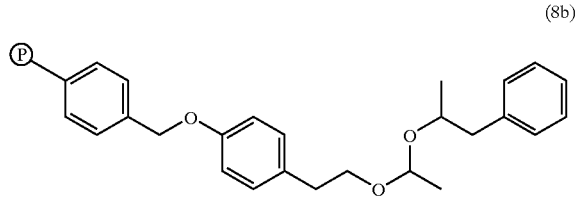

(8b)

To resin having vinyl ether linker of formula 1a (340.0 mg, 0.5 mmol) in 1,2-dichloroethanol (8 ml) was added pyridinium ρ-toluenesulfonate (25.0 mg, 0.1 mmol). 1-Phenyl-2-propanol (204.0 mg, 1.5 mmol) was added and then performed as in the preparation of the compound of formula 8a to obtain light brown resin of the desired product of formula 8b (379.0 mg).

ii-2) Cleavage of Alcohol from 1-phenyl-2-propanol Resin of Formula 8b

The obtained resin of formula 8b (379.0 mg) was added to 1.5% HCl/MeOH solution (15 ml) and stirred for 5 hrs at room temperature. The reaction mixture was filtered and filtrate was evaporated to obtain 1-phenyl-2-propanol (42.0 mg, yield 62%; 3-steps from Merrifield resin).

$^1$H NMR(200 MHz, CDCl$_3$): δ 7.36–7.20 (m, 5H), 4.05–3.99 (m, 1H), 2.83-2.63 (m, 2H), 1.25 (d, 3H, J=6.2 Hz)

iii-1) Introduction of N-hydroxymethyl Phthalimide

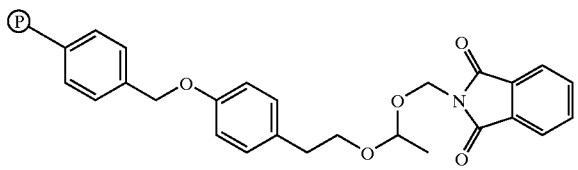

(8c)

To resin having vinyl ether linker of formula 1a (340.0 mg, 0.5 mmol) in 1,2-dichloroethanol (8 ml) was added pyridinium ρ-toluenesulfonate (25.0 mg, 0.1 mmol). N-Hydroxymethyl phthalimide (266.0 mg, 1.5 mmol) was added and then performed as in the preparation of the compound of formula 8a to obtain light brown resin of the desired product of formula 8c (392.0 mg).

IR(KBr): 1706 cm$^{-1}$ iii-2) Cleavage of Alcohol from N-hydroxymethyl Phthalimide Resin of Formula 8c The obtained resin of formula 8c (392.0 mg) was added to 1.5% HCl/MeOH solution (15 ml) and stirred for 5 hrs at room temperature. The reaction mixture was filtered and filtrate was evaporated to obtain N-hydroxymethyl phthalimide (47.0 mg, yield 53%; 3-steps from Merrifield resin).

$^1$H NMR(200 MHz, CDCl$_3$): δ 7.91–7.84 (m, 2H), 7.79–7.73 (m, 2H), 5.25 (s, 2H)

iv-1) Introduction of 4-phenyl Phenol

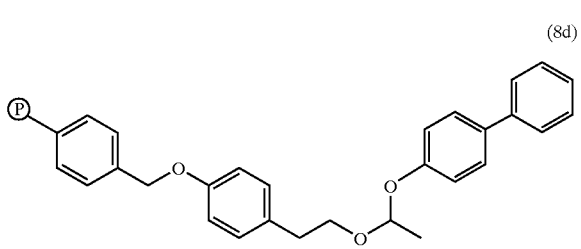

(8d)

To resin having vinyl ether linker of formula 1a (340.0 mg, 0.5 mmol) in 1,2-dichloroethanol (8 ml) was added pyridinium ρ-toluenesulfonate (25.0 mg, 0.1 mmol). 4-Phenyl phenol (255.0 mg, 1.5 mmol) was added and then performed as in the preparation of the compound of formula 8a to obtain light brown resin of the desired product of formula 8d (387.0 mg).

iv-2) Cleavage of Alcohol from 4-phenyl Phenol Resin of Formula 8d

The obtained resin of formula 8d (392.0 mg) was added to 1.5% HCl/MeOH solution (15 ml) and stirred for 5 hrs at room temperature. The reaction mixture was filtered and filtrate was evaporated to obtain 4-phenyl phenol (51.0 mg, yield 60%; 3-steps from Merrifield resin).

$^1$H NMR(200 MHz, CDCl$_3$): δ 7.57–7.25 (m, 7H), 6.91 (d, 2H, J=8.6 Hz)

EXAMPLE 3

Introduction and Cleavage of Nitrogen-containing Hetero Cyclic Compound to/from the Resin Having Vinyl Ether Linker of Formula 1 i-1) Introduction of Purine Group

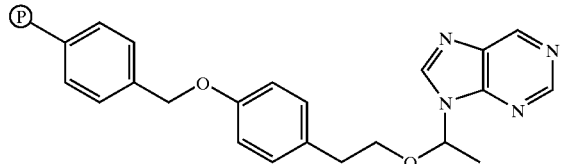

(8e)

To resin having vinyl ether linker of formula 1a (340.0 mg, 0.5 mmol) in 1,2-dichloroethanol (8 ml) was added champhorsulfonic acid (23.0 mg, 0.1 mmol). Purine (180.0 mg, 1.5 mmol) was added and stirred for 24 hrs at room temperature. The reaction mixture was filtered and filtrate was washed with CH$_2$Cl$_2$, DMF, DMF/H$_2$O, H$_2$O and MeOH several times to obtain light brown resin of formula 8e (369.0 mg).

i-2) Cleavage of Purine from Purine Resin of Formula 8e

The obtained resin of formula 8e (369.0 mg) was added to 1.5% HCl/MeOH solution (15 ml) and stirred for 5 hrs at room temperature. The reaction mixture was filtered and filtrate was evaporated to obtain purine salt (35.0 mg, yield 45%; 3-steps from Merrifield resin).

$^1$H NMR(200 MHz, CD$_3$OD): δ 9.57 (s, 1H), 9.34 (s, 1H), 9.10 (s, 1H)

ii-1) Introduction of 5-(4-ρ-toluyl)phenyl Tetrazole of Formula 8f

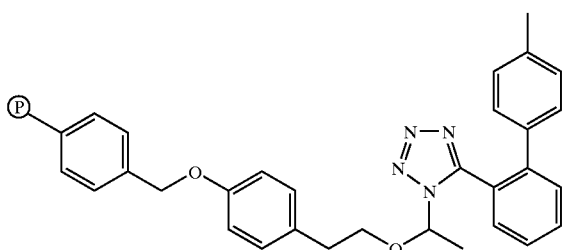

(8f)

To resin having vinyl ether linker of formula 1a (340.0 mg, 0.5 mmol) in 1,2-dichloroethanol (8 ml) was added trifluoroacetic acid (11.4 mg, 0.1 mmol). 5-(4-p-Toulyl) phenyl tetrazole (354.0 mg, 1.5 mmol) was added and stirred for 24 hrs at room temperature. The reaction mixture was filtered and filtrate was washed with CH$_2$Cl$_2$, DMF, DMF/H$_2$O, H$_2$O and MeOH several times to obtain light brown resin of formula 8f (413.0 mg).

IR(KBr): 1119, 1029 cm$^{-1}$ i-2) Cleavage of the Tetrazole Group from 5-(4-p-toulyl) phenyl Tetrazole Resin of Formula 8f The obtained resin of formula 8f (413.0 mg) was added to 1.5% HCl/MeOH solution (15 ml) and stirred for 5 hrs at room temperature. The reaction mixture was filtered and filtrate was evaporated to obtain tetrazole compound (95.0 mg, yield 85%; 3-steps from Merrifield resin).

$^1$H NMR(200 MHz, CD$_3$OD) δ 7.66–7.51 (m, 4H), 7.11 (d, 2H, J=8.2 Hz), 6.98 (d, 2H, J=8.0 Hz), 2.32 (s, 3H)

EFFECT OF THE INVENTION

As shown in Examples, the resin having vinyl ether linker of the present invention is useful for the organic syntheses of hetero atom-containing compounds such as alcohols, thiols, imidazoles, triazoles and tetrazoles by employing combinatorial chemical synthesis on solid-phase supports. Accordingly, the present invention provides excellent application in combinatorial chemical synthesis on solid-phase support and a simple tool for discovering lead compounds and optimizing the molecular structure and functions thereof.

What is claimed is:

1. A resin having vinyl ether linker expressed by formula (1) useful as a solid-phase support in combinatorial chemical synthesis,

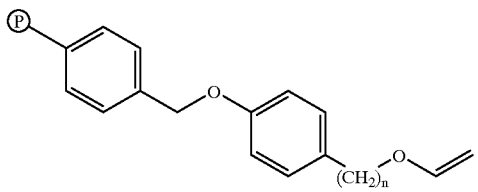
(1)

wherein Ⓟ is polystyrene-divinylbenzene; and n is an integer of 1 to 5.

2. A process for preparing a resin having vinyl ether linker of formula (1) comprising:

(a) a reduction of methyl(4-hydroxybenzyl)ester of formula (2) to 4-hydroxyphenethyl alcohol of formula (3);

(b) a reaction of the obtained 4-hydroxyphenethyl alcohol of formula (3) with ethylvinyl ether of formula (4) to produce 4-(2-vinyloxyethyl)phenol of formula (5); and (c) a reaction of the obtained 4-(2-vinyloxyethyl)phenol of formula (5) with Merrifield resin of formula (6) to produce the resin having vinyl ether linker expressed by formula (1),

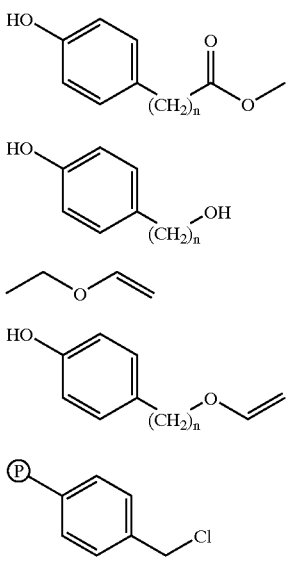

3. A process for preparing the resin having vinyl ether linker of formula (1) according to claim 2, wherein said (b) reaction introducing vinyl ether group to the compound of formula (3) is performed in the presence of mercury acetate catalyst.

4. A process for preparing the resin having vinyl ether linker of formula (1) according to claim 2, wherein said (c) reaction introducing the compound of formula (5) to Merrifield resin is performed in the presence of a base catalyst.

5. A process for preparing the resin having vinyl ether linker of formula (1) according to claim 4, wherein said base catalyst is selected from the group consisting of sodium alkoxide and sodium hydride.

6. An organic synthesis on solid-phase support, comprising introducing a hetero atom-containing compound of formula (7) using a resin having vinyl ether linker of formula (1) as a solid support, performing multi-step reaction, and cleaving the hetero atom-containing compound of formula (7) from the solid support,

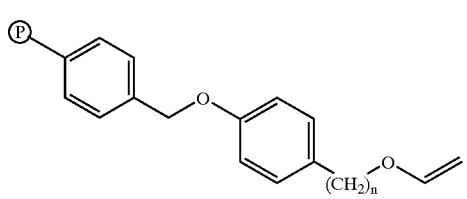
(1)

HY—(CH$_2$)$_m$—X    (7)

wherein Ⓟ is polystyrene-divinylbenzene;

Y is O or NH;

X is H, OH, SH, a halogen atom, phenyl, phenyl or biphenyl substituted with halogen atom(s), or

formed by bonding another hetero atom (X') with Y, where Y and X' are independently from 1 to 5 hetero atoms and the bonding is chosen from C$_1$–C$_4$ alkylenes and alkenyls; and M is an integer of 1 to 4.

7. An organic synthesis on solid-phase support according to claim 6, wherein said compound of formula (7) is selected from the group consisting of 4-bromobenzyl alcohol, 1-phenyl-2-propanol, 4-phenylphenol, N-hydroxymethyl phthalimide, purine and 4-(p-toulyl)phenyl tetrazole.

8. An organic synthesis on solid-phase support according to claim 6, wherein said reaction of introducing a hetero atom-containing compound of formula (7) on the resin having vinyl ether linker of formula (1) is performed in the presence of an acid catalyst.

9. An organic synthesis on solid-phase support according to claim 8, wherein said acid catalyst is selected from the group consisting of champhorsulfonic acid, trifluoroacetic acid and pyridium ρ-toulenesulfonate.

10. An organic synthesis on solid-phase support according to claim 6, wherein said reaction of cleaving the hetero atom-containing compound of formula (7) from the resin having vinyl ether linker of formula (1) is performed in the presence of an acid catalyst and anhydrous organic solvent.

11. An organic synthesis on solid-phase support according to claim 10, wherein said acid is hydrochloric acid in methanol.

12. A resin having vinyl ether linker expressed by formula (1) useful as a solid-phase support in combinatorial chemical synthesis,

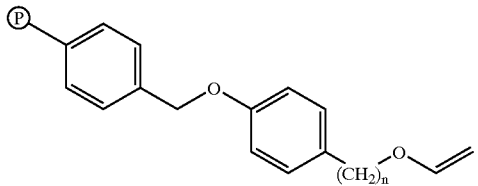

(1)

wherein Ⓟ is a resin; and n is an integer of 1 to 5.

13. An organic synthesis on solid-phase support, comprising introducing a hetero atom-containing compound of formula (7) using a resin having vinyl ether linker of formula (1) as a solid support, performing a multi-step reaction, and cleaving the hetero atom-containing compound of formula (7) from the solid support,

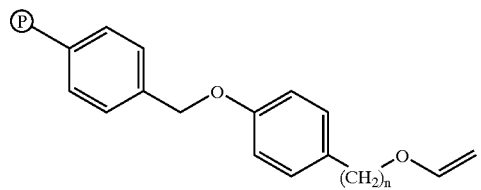

(1)

$$HY\text{—}(CH_2)_m\text{—}X \quad (7)$$

wherein Ⓟ is resin;

Y is O or NH;

X is H, OH, SH, a halogen atom, phenyl, phenyl or biphenyl substituted with halogen atom(s), or

formed by bonding another hetero atom (X') with Y, where Y and X' are independently from 1 to 5 hetero atoms and the bonding is chosen from $C_1$–$C_4$ alkylenes and alkenyls; and M is an integer of 1 to 4.

\* \* \* \* \*